United States Patent [19]
Dickie et al.

[11] Patent Number: 5,465,709
[45] Date of Patent: Nov. 14, 1995

[54] ILLUMINATED VAGINAL SPECULUM

[75] Inventors: Robert G. Dickie, Newmarket; Michael J. Phillips, Mississauga, both of Canada

[73] Assignee: Advanced Medical Products Inc., King City, Canada

[21] Appl. No.: 150,521

[22] Filed: Nov. 10, 1993

[51] Int. Cl.$^6$ ................................ A61B 1/06; A61B 1/32
[52] U.S. Cl. ................................................................ 600/223
[58] Field of Search ........................ 128/18, 17, 16, 128/13, 11, 9, 23; 362/34, 396

[56] References Cited

U.S. PATENT DOCUMENTS

| | | | |
|---|---|---|---|
| 2,599,303 | 6/1952 | Ward | 362/396 X |
| 3,716,047 | 2/1973 | Moore et al. | 128/18 |
| 3,900,924 | 8/1975 | Meltzner | 128/16 X |
| 4,290,422 | 9/1981 | Burton | 128/23 |
| 4,337,763 | 7/1982 | Petrassevich | 128/11 X |
| 5,179,938 | 1/1993 | Lonky | 128/18 |
| 5,231,973 | 8/1993 | Dickie | 128/17 |
| 5,277,173 | 1/1994 | Cantele | 128/11 |

*Primary Examiner*—Richard J. Apley
*Assistant Examiner*—Beverly M. Flanagan

[57] ABSTRACT

A single use, disposable, vaginal speculum uses a chemically florescent light tube to provide built-in illumination for the body cavity being examined with the speculum. An integrally molded light tube holder has two opposing walls between which the light tube is inserted. Ridges on the inner surfaces of the opposing walls serve to guide the light tube into position in the speculum and to firmly grasp the light tube so as to prevent dislodgement during the examination. An integral stop member is molded into the light tube holder to terminate the insertion of the light tube into the holder in precisely the position required to properly position the light tube.

3 Claims, 2 Drawing Sheets

ILLUMINATED VAGINAL SPECULUM

TECHNICAL FIELD

This invention relates to medical specula and, more particularly, to an illuminated, single use, disposable vaginal speculum.

BACKGROUND OF THE INVENTION

In order to facilitate the examination of internal body cavities with an external orifice, it is sometimes necessary to employ an instrument to dilate the orifice in order to see into the cavity. Such instruments are called specula. Specula for examination of the cervix employ a pair of paddles or blades which are inserted into the vagina. The paddles are then separated to dilate the vaginal orifice and permit examination of the cervix.

It is extremely useful to illuminate the interior of the cavity being examined with a speculum in order to facilitate examination. The prior art has relied on light sources mounted on the speculum or supported separately from the speculum and arranged to direct light into the cavity being examined. Such light sources are expensive, clumsy and difficult to integrate into single-use, throw away disposable specula. One prior art patent, W. C. Moore et al U.S. Pat. No. 3,716,047, granted Feb. 13, 1973, discloses a speculum with a curved light bar within one of the paddles of the speculum which guides light, by internal reflection, from a light source in the handle, toward the cavity being examined. Such a guided light illumination means adds significantly to the cost of the speculum as well as increasing its size and weight. Moreover, the accommodation of a light source detracts from the disposable nature of the balance of the speculum.

SUMMARY OF THE INVENTION

In accordance with the illustrative embodiment of the present invention, these and other problems are overcome by an improved speculum with a built-in accommodation for a disposable light source. More particularly, a florescent light tube which produces light by chemical interaction is adapted for attachment to a injection molded speculum such that the combination of speculum and light source can be thrown away after a single use. Even more particularly, a pair of retention walls or blades on one paddle of the speculum are separated by a distance slightly less than the diameter of the light tube, thereby facilitating the attachment of the light tube to the paddle. The light tube is slightly deformed when pressed between the retention wall to increase the frictional hold of the walls on the light tube. This separation of the retention walls also accommodates a realistic range in the expected diameters of the light tubes as well as a range of "out-of-roundness" dimensions of available light tubes. A positive deformation of the light tube has therefore been found to be essential for insuring adequate retention characteristics. The placement of these retention walls or blades on the upper dilator paddle has been found to minimize the interference with the line of sight of the examining physician.

In accordance with one feature of the present invention, the interior surfaces of the retention walls have one or more ridges formed therealong with the apex of the ridge further grasping the light tube. The danger of the light tube becoming disengaged and failing into the cavity being examined is thereby diminished. In accordance with another feature of the present invention, these interior ridges on the retention walls are sloped downward toward the base of the retention walls to assist in guiding the light tube into a fully engaged position between the retention walls. The angle of these ridges with respect to the axis of the paddle on which they are molded can vary between as little as thirty degrees to as much as ninety degrees and still maintain their dual function of enhancing retention of the light tube and guiding the light tube into operating position. It is to be noted that the direction of these interior ridges must be in the direction of the parting of the injection mold halves to permit economical fabrication. The height of these interior ridges away from the surface of the retention walls is between 0.005 and 0.020 inches, and preferably 0.015 inches, to provide adequate retaining characteristics. Between three and five such ridges have been found to be optimal in insuring adequate retention of the light tube. The deformation of the light tube is much more readily accomplished at contact points of limited area, as provided by the interior ridges on the retention walls.

In accordance with yet another feature of the present invention, a stopping member is formed between the two retention ridges with a shoulder that acts as a stop for the light tube. This shoulder stop ensures the positioning of the light tube in an optimum position for casting light into the interior of the cavity being examined. This light tube stop need only be high enough to engage the light tube so as to prevent further movement between the retention walls. The light tube stop is positioned such that only a fraction of the light tube is engaged by the retention walls, thereby leaving a large portion of the light tube exposed so as to maximize the amount of light cast into the cavity being examined, as well as further minimizing the interference of such retention walls with the line of sight of the examining physician.

BRIEF DESCRIPTION OF THE DRAWINGS

A complete understanding of the present invention may be gained by considering the following detailed description in conjunction with the accompanying drawing, in which.

To facilitate reader understanding, identical reference numerals are used to designate elements common to the figures.

DETAILED DESCRIPTION

Figure 1:
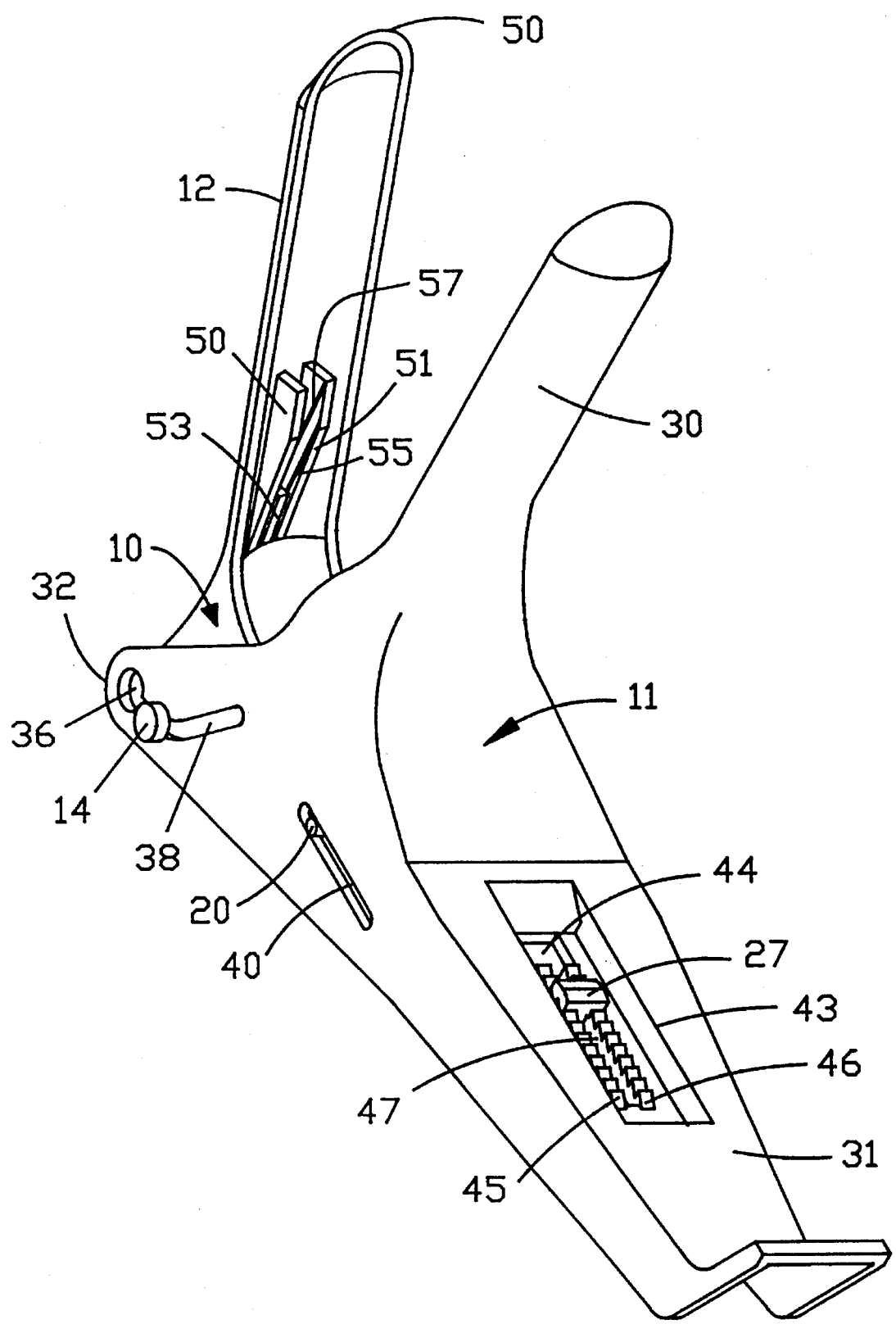
FIG. 1 shows a perspective view of a molded plastic single-action speculum having a holder for a self-contained chemically florescent light tube illumination source molded therein in accordance with the present invention.

Referring more particularly to FIG. 1, there is shown a perspective view of a plastic vaginal speculum in accordance with the present invention comprising an upper paddle member 10 and a lower paddle member 11. Upper paddle member 10 comprises a dilator blade or paddle 12 designed to be inserted into the vaginal opening for purposes of examination. Paddle 12 has a rounded nose 50 and a base member, not shown in FIG. 1, including, at the lateral extremities of the base member are cam follower pins, only one of which is show in FIG. 1 as to pin 14, having enlarged heads and smaller diameter follower surfaces. In operation, pin 14 rides in cam slot 38 to provide the relative opening movement between paddles 12 and 30. Situated below pin 14 is a retention pin 20 which slides in lineal slot 40.

Lower paddle member 11 comprises a lower dilator blade or paddle 30 attached to a handle 31 formed with three sides of plastic material. At the upper end of handle 31 are two extensions only one of which is shown in FIG. 1 as extension 32, each of which includes a cam slot only one of which is shown in FIG. 1 as cam slot 38. Cam slot 38 has an upper round opening 36 sufficiently large to accommodate the enlarged head of cam follower pin 14 and thus permit assembly of the two paddle members 10 and 11 together. Below cam slot 38 is a matching vertical retention slot 40. Pin 20 fits into slot 40 to trap the lower portion of upper paddle member 10 in sliding contact with the rear face of handle 31.

In the front face of handle 31 is an elongated vertical recess 43 having a rectangular opening 44 at the top which accommodates pawl 27. At either side of a central slot 47 in recess 43 are a pair of ratchet bars 45 and 46 which can be engaged by toothed surfaces on the rear of pawl 27. Not shown in FIG. 1 is a spring-loaded thumb pad on the back of paddle member 10 which is attached to pawl 27 which, when depressed, disengages pawl 27 from toothed ratchet bars 45 and 46. Central slot 47 permits pawl 27 to slide between ratchet bars 45 and 46 to permit locking the paddle members 10 and 11 in any relative position desired.

Upper paddle member 10 is assembled to lower paddle member 11 by inserting pawl 27 through opening 44. Simultaneously, extension 32 and a matching extension of the other side of paddle member 11 are spread laterally sufficiently to insert cam follower 14 and a mating cam follower into holes corresponding to opening 36 in extension 32. At the same time, pin 20 is inserted into slots in member 11 corresponding to slot 40. Once assembled in this manner, by depressing a thumb pad not shown in FIG. 1, the upper paddle member 10 can be made to slide down on lower paddle member 11 until pawl 27 reaches the bottom of slot 47, pin 20 reaches the bottom of slot 40 and cam follower pin 14 reaches the bottom of cam slot 38. In this position, the paddles 12 and 30 are dosed on each other and the vaginal specula of FIG. 1 is completely assembled for packaging, storage and shipping. Depressing the thumb pad and sliding paddle member 10 upward with respect to paddle member 11 causes paddles 12 and 30 to open up to whatever separation is required for the pelvic examination.

In accordance with the present invention, a pair of light tube retention walls or blades 50 and 51 are attached to the underside of the upper paddle 12 of the vaginal speculum of FIG. 1. Walls or blades 50 and 51 are dimensioned and positioned to receive a cylindrical plastic florescent light tube of the type which emits light when a membrane is broken to allow two chemical reservoirs to intermix their contents. Such light tubes may also have one or both ends formed into a lens to assist in concentrating the light emitted by the chemicals in the tube. The light tube or "lightstick" consists of two separate chemical components, an outer oxalate component encapsulated by a durable polypropylene casing and an inner "activator" component encased in a glass ampule that floats within the oxalate. The light tube is "activated" to produce light by flexing the polypropylene casing to fracture the glass ampule, allowing the two chemical components to mix. The glass ampule remains completely enclosed in the polypropylene casing both before and after activation. Such light tubes can be obtained from American Cyanimid Company under the trade name "SPECULITE®".

As received from the manufacturer, such light tubes vary considerably in degree of roundness and in diameter. It is necessary to firmly grasp the light tube in the upper paddle 12 of FIG. 1 to prevent its dislodgement during use which would result in loss of adequate light to do the desired examination and even possibly deposit of the light tube into the cavity being examined. Retention walls 50 and 51 are therefore separated by a dimension somewhat smaller than the average diameter of the light tube to accommodate the expected variation in tube diameter and out-of-roundness. It will be noted that retention walls 50 and 51 are located near the inner end of paddle 12 which, when in use, are near the outer orifice of the cavity being examined. This placement facilitates lighting the entire cavity.

Figure 4:
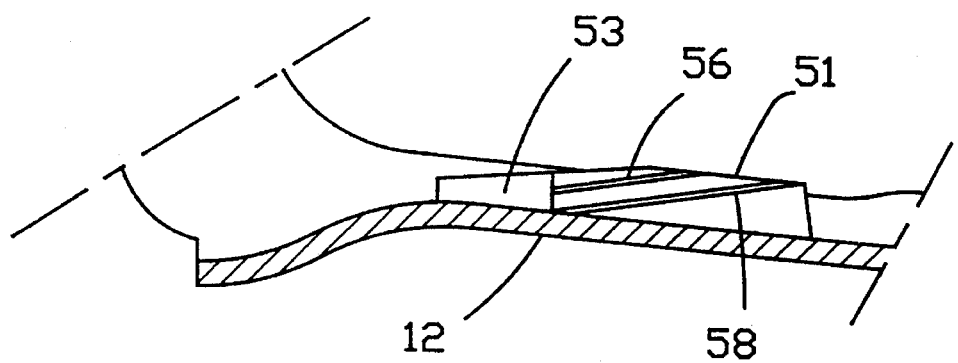
FIG. 4 is a longitudinal cross-sectional view of the upper paddle of the vaginal speculum shown in FIG. 3 showing more details of the light tube holder shown in perspective in FIG. 2.

In order to further facilitate retention of the light tube between walls 50 and 51, one or more ridges 55, 56, 57, 58 are formed on the inner surfaces of walls 50 and 51. These ridges 55–58, better seen in FIG. 4, are between 0.005 inches and 0.020 inches in height off of the walls 50 and 51, and preferably around 0.015 inches. This height constricts the area for grasping the light tube, thereby reducing the force necessary to position the light tube between the walls 50–51 and, at the same time, increasing the retention force. Ridges 55–58 are formed at an angle to paddle 12 to assist in guiding the light tube towards the inner surface of paddle 12. This angle facilitates the proper positioning of the light tube between the walls 50–51. While the preferred embodiment includes between three and five sets of opposing ridges like ridges 55–58, only two such pairs of ridges have been illustrated in the drawings to simplify the drawing and render it more readable.

A third rib or shoulder 53 is attached to the underside of paddle 12 between walls 50 and 51 and positioned to act as a stop for the light tube. That is, the light tube is pushed between walls 50 and 51 from the open end until the inserted end of the light tube engages rib 53. Rib 53 is positioned to limit the insertion of the light tube sufficiently so that the majority of the length of the light tube extends beyond the open end of the canyon formed by walls 50–51, thus maximizing the amount of light with an unrestricted path to the interior of the cavity being examined. The number of ridges 55–58 which can be formed on the inner surfaces of walls 50–51 is between one and five, and, as previously noted, preferably between three and five. It will be noted that the cavity molds used for injection molding of the upper paddle member 10 must open along a path parallel to the ridges 55–58 to prevent blocking the removal of the parts of the mold from the molded paddle member when the material of the paddle member within the mold has solidified.

The vaginal speculum of FIG. 1 can be fabricated of metal, preferably stainless steel, and be reused as often as desired by sterilizing between uses. In the preferred embodiment, however, the entire instrument is made of plastic and is sufficiently inexpensive to be discarded after only one use. One standard grade sterile plastic is known as CYCOLAC HP-20, manufactured by the General Electric Company. Alternatively, a reusable plastic such as LEXAN® HPS-1 Transparent, also manufactured by the General Electric Company, can be used and the plastic speculum sterilized in an autoclave between up to ten successive uses. The basic articulated vaginal speculum described in FIG. 1 is disclosed in more detail in R. G. Dickie U.S. Pat. No. 5,231,973 granted Aug. 3, 1993. The details of the light tube retention structure is disclosed in FIGS. 2 through 4.

Figure 2:
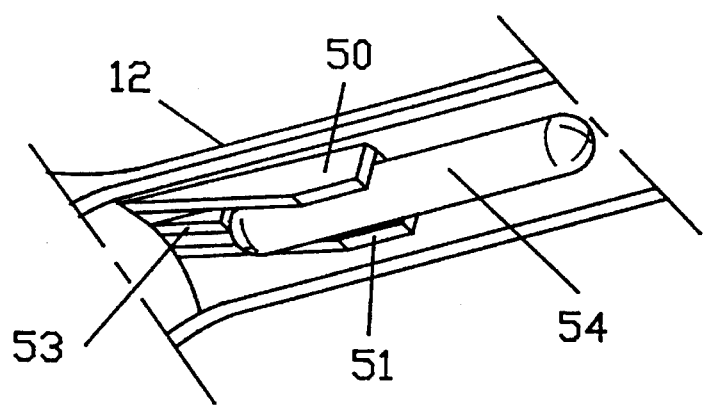
FIG. 2 is a more detailed perspective view of the light tube and light tube holder molded into the upper paddle of the vaginal speculum illustrated in FIG. 1.

In FIG. 2 there is shown a larger scale perspective view of the light tube retention structures shown in FIG. 1 and including the light tube 54 secured in position between the retention walls 50 and 51 molded on the inner surface of upper paddle 12. As can be seen in FIG. 2, stop 53 controls the positioning of light tube 54 such that over half of the length of light tube 54 extends outside of the canyon formed by walls 50–51. This minimizes the interference of walls 50–51 with the transmission of light from the light tube 54 to the interior of the cavity being examined.

Figure 3:
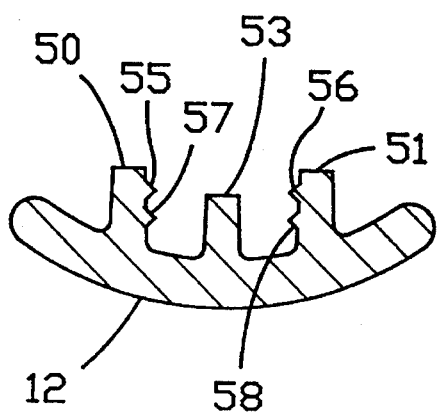
FIG. 3 is a lateral cross-sectional view of the upper paddle of the vaginal speculum illustrated in FIG. 2 showing the detailed cross-section of the light tube holder shown in perspective in FIG. 2.

In FIG. 3 there is shown a transverse cross sectional view through the upper paddle member 12 at the location of the retention walls 50 and 51. It can be seen that the inner surfaces of walls 50 and 51 have matching sets of retention ridges 55–56 and 57–58, two on each respective one of walls 50 and 51. As previously noted, ridges 55–58 are between 0.005 and 0.020 inches and can be between one and five in number. As has been previously noted, only two ridges are illustrated on each of walls 50 and 51 to simplify the drawings. As can be seen clearly in FIG. 3, a stop 53 is located between walls 50 and 51 which serves the purpose of stopping the insertion of light tube 54 (FIG. 2) between walls 50 and 51. As can be seen in FIG. 3, stop 53 need not be as high as walls 50 and 51 and, indeed, need only be high enough to act as a stop for light tube 54.

In FIG. 4 there is shown a longitudinal cross sectional view through the upper paddle member 12 of the vaginal speculum of FIG. 1. As can be seen in FIG. 4, wall 51 includes a plurality of ridges 56 and 58 which grasp a light tube such as light tube 54 in FIG. 2 and prevent the light tube from becoming disengaged and falling into the cavity being examined. Stop 53 is seen as terminating the insertion of the light tube so as to position the light tube in the most advantageous position for shedding light into the cavity being examined. In FIG. 4 it can be seen that ridges 56 and 58 are oriented at an angle to the portion of paddle 12 where wall 51 is attached. This angle can vary between thirty degrees and ninety degrees and serves the purpose of guiding the light tube toward the interior surface of paddle 12, thereby ensuring the proper positioning of the light tube once it is inserted between walls 50 and 51. It is to be noted that, if the upper paddle member 10 (FIG. 1) is fabricated by an injection molding process, then the mold half facing the concave underside of paddle 12 must be withdrawn away from the molded paddle member 10 in a direction parallel to ridges 55–58 to prevent either breaking ridges 55–58 or locking the the mold half to the molded paddle. The angle at which ridges 55–58 are disposed with respect to paddle 12 is therefore a compromise between the optimum angle for guiding the light tube into position and the optimum angle for withdrawing the mold half from the molded product. As noted above, this angle can be varied between 30 and 90 degrees, but is preferably near the lower end of this range.

It can be seen that the light tube holder of the present invention ensures not only the proper positioning of the light tube for casting the maximum amount of light into the cavity being examined, but also ensures easy insertion of the light tube into the light tube holder and positive retention of the light tube in the holder so as to prevent the light tube from falling into the cavity being examined. The integrated light tube holder facilitates the fabrication of a single use, disposable speculum with self-illumination forming an integral part of the speculum. The retention ridges assist in both positioning the light tube and also in retaining the light tube in position. An integral stop further improves the positioning of the light tube while, at the same time, making the insertion of the light tube into position easily accomplished by the examining physician.

It should also be clear to those skilled in the art that further embodiments of the present invention may be made by those skilled in the art without departing from the teachings of the present invention.

What is claimed is:

1. A speculum comprising a first paddle member having a longitudinal axis, an interior surface, and an exterior surface;

a second paddle member opposite and operatively associated with said first paddle member, said second paddle member having a longitudinal axis, an exterior surface and an interior surface wherein the interior surfaces of said first and second paddle members are positioned in opposite spaced relation to each other, said first and second paddle members being adapted for insertion into and dilation of the opening of a body cavity so as to permit examination of the interior of the body cavity;

a light tube holder for retaining a chemically florescent light tube, said light tube holder comprising two planar retention walls positioned in opposite spaced relation on one of said interior surfaces and extending outwardly therefrom, each of said retention walls having a proximal edge, an inner planar surface, an outer planar surface, said inner and outer surfaces extending between said proximal and distal edges, and at least one ridge, said at least one ridge extending outwardly from said inner surface and being disposed at an angle to the longitudinal axis of said one of said interior surfaces.

2. The speculum according to claim 1, further comprising a chemically florescent light tube positioned between said retention walls, said light tube having an average diameter that is greater than the distance between said two retention walls.

3. The speculum according to claim 1, wherein said angle is between thirty and ninety degrees.

\* \* \* \* \*